United States Patent [19]

Tezuka et al.

[11] Patent Number: 4,869,788
[45] Date of Patent: Sep. 26, 1989

[54] DENTAL DIAMOND BAR AND MANUFACTURING METHOD THEREOF

[75] Inventors: Satoshi Tezuka; Kanji Matsutani, both of Tochigi, Japan

[73] Assignee: Matsutani Seisakusho Company, Ltd., Takanezawa, Japan

[21] Appl. No.: 209,305

[22] Filed: May 25, 1988

Related U.S. Application Data

[62] Division of Ser. No. 141,494, Jan. 7, 1988.

[30] Foreign Application Priority Data

Mar. 24, 1987 [JP] Japan .................................. 62-67886

[51] Int. Cl.⁴ .............................................. C25O 5/02
[52] U.S. Cl. .......................................... 204/15; 204/16
[58] Field of Search .................................... 204/15, 16

[56] References Cited

U.S. PATENT DOCUMENTS 3,046,204 7/1962 Barron .................................... 204/16
4,078,906 3/1978 Green ..................................... 51/295

FOREIGN PATENT DOCUMENTS 2167575 8/1973 France .
1151323 5/1969 United Kingdom .
2154487 9/1985 United Kingdom .

Primary Examiner—T. M. Tufariello
Attorney, Agent, or Firm—Wegner & Bretschneider

[57] ABSTRACT

A dental diamond bar comprising a grinding section which has diamond abrasive grains electrodeposited on an outer peripheral surface of a forward end portion of a bar body. A paint-applied section has a colored paint applied to an outer peripheral surface of a part of the bar body. The paint-applied section is located adjacent a rearward edge of the grinding section. In a method of manufacturing the diamond bar, the colored paint is applied to the bar body to form the paint-applied section. Masking liquid is applied to the bar body to form a masking section. The masking section has a forward edge which is located between forward and rearward edges of the paint-applied section. The masking section extends from the paint-applied section toward a rearward end of the bar body. The masking section is removed after formation of the grinding section.

10 Claims, 5 Drawing Sheets

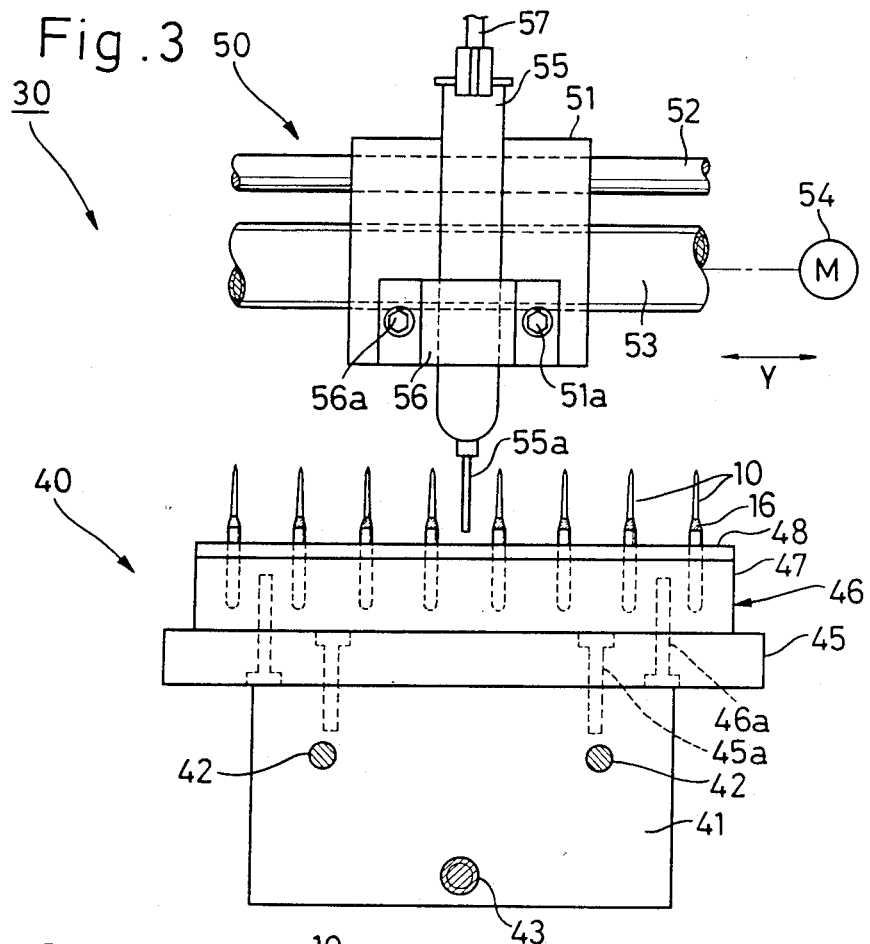
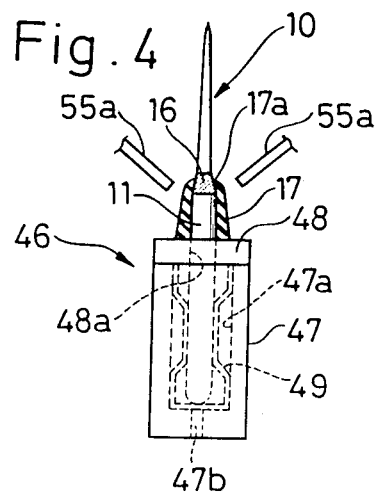
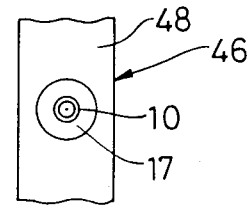

DENTAL DIAMOND BAR AND MANUFACTURING METHOD THEREOF

This application is a divisional of Ser. No. 141,494, filed Jan. 7, 1988.

BACKGROUND OF THE INVENTION

The present invention relates to a dental diamond bar having electrodeposited thereon diamond abrasive grains and a manufacturing method suitable for the diamond bar.

A conventional diamond bar employed in dental treatment comprises a bar body having a rearward end portion formed into a shank portion. Diamond abrasive grains are fixedly bonded to, i.e., electrodeposited on a peripheral surface of a forward end portion of the bar body by a plating layer of metal such as nickel or the like, to form a grinding section. An annular groove is formed at an axially intermediate section of the shank portion. Colored paint is applied to the annular groove. The color of the applied paint enables a user to identify the type or kind of the diamond bar, that is, configuration of the grinding section, grain size of the abrasive grains and the like.

In the above-described diamond bar, however, since the identifying colored paint is applied to the axially intermediate section of the shank portion, it is not easy to ascertain the type or kind of the diamond bar. The reason for this is that once the shank portion of the diamond bar is fitted into a handpiece, the paint is concealed by the handpiece and cannot be seen. Also when the shank portions of the respective diamond bars are inserted respectively into a plurality of bores formed in a storage bar stand to store the diamond bars, the paints on the respective shank portions are concealed by the stand and cannot be seen. Further, it is required to form the annular groove in the shank portion in order for the paint thereon not to interfere with insertion of the shank portion into the handpiece. This correspondingly increases the manufacturing cost of the diamond bar.

The diamond bar constructed as described above is manufactured in the following manner. That is, a bar body is first prepared which comprises a shank portion having an axial intermediate section formed therein with an annular groove. The bar body further comprises a grinding-section scheduled part which extends from the shank portion to the forward end of the bar body. Subsequently, an electrically insulating material is applied to a part of the bar body which extends from the grinding-section scheduled part toward the rearward end of the bar body, to form a masking section. Then, a forward end portion of the bar body including the grinding-section scheduled part is driven into a multiplicity of diamond grains immersed in electrolytic solution containing nickel ions, to electrodeposit the diamond grains onto the grinding-section scheduled part, whereby the grinding section is formed. Since the diamond grains are not electrodeposited on the masking section of the bar body, the rearward edge of the grinding section is brought into conformity with the forward edge of the masking section. Subsequently, the masking section is removed, and then colored paint is applied to the annular groove. Thus, the dental diamond bar is obtained as a final product.

Japanese Patent Application Laid-Open No. 62-49845 has been filed by the same assignee as that of the present invention and has been laid open to public inspection on Mar. 4, 1987. The Japanese patent discloses a technique of the above-mentioned masking in which bar bodies are dipped into masking liquid to form masking sections on the respective bar bodies. The masking technique is superior in operability. However, the forward edge of the masking section is often unstable in position, so that the rearward edge of the grinding section might not be constant in position, or might wave or undulate when the bar body is viewed in side elevation. This would result in a variation in length of the grinding section from product to product, and a variation in configuration of the rearward edge of the grinding section from product to product.

The above-mentioned Japanese patent describes, as the prior art, a technique of applying masking liquid to a bar body by means of a brush to form a masking section on the bar body. It is possible for such masking technique to correctly determine the forward edge of the masking section, so that the position of the rearward edge of the grinding section can be made constant. Thus, the rearward edge of the grinding section can be made straight when the bar body is viewed in side elevation. However, the masking technique is extremely low in operating efficiency, because the masking is effected manually.

The above-mentioned Japanese patent also describes, as the prior art, a masking technique in which an insulating tape is wrapped about a bar body. Such masking technique has advantages and disadvantages similar to those of the above-described masking technique in which the masking liquid is applied to the bar body by means of a brush.

SUMMARY OF THE INVENTION

It is an object of the invention to provide a dental diamond bar in which it is possible to clearly identify the type or kind of the diamond bar even after the diamond bar is fitted in a handpiece or the like, and the diamond bar is inexpensive.

It is another object of the invention to provide a method of manufacturing a dental diamond bar, which can manufacture the diamond bar efficiently, in which it is possible to prevent waving or undulating of a rearward edge of a grinding section, and to prevent occurrence of a variation in length of the grinding section, and in which productivity can considerably be improved.

According to the invention, there is provided a dental diamond bar comprising a bar body, a grinding section formed on an outer peripheral surface of a forward end portion of the bar body, the grinding section having diamond abrasive grains electrodeposited on the outer peripheral surface of the forward end portion of the bar body, and a paint-applied section having a colored paint applied to an outer peripheral surface of a part of the bar body, in which the paint-applied section is located adjacent a rearward edge of the grinding section.

According to the invention, there is further provided a method of manufacturing a dental diamond bar comprising the steps of:

applying an electrically insulating colored paint to an outer peripheral surface of an intermediate section of a bar body to form a paint-applied section so as to bring the paint-applied section correctly into conformity with a predetermined axial area on the intermediate section;

applying masking liquid formed of an electrical insulating material to the bar body, and solidifying the masking liquid to form a masking section, the masking section having a forward edge located between forward and rearward edges of the paint-applied section, the masking section extending toward a rearward end of the bar body;

fixedly bonding diamond abrasive grains to a part of the bar body extending from the forward edge of the paint-applied section to a forward end of the bar body, by an electrodeposition technique, to form a grinding section; and removing the masking section after formation of the grinding section.

BRIEF DESCRIPTION OF THE DRAWINGS

FIG. 3 is a side elevational view of the masking apparatus illustrated in FIG. 2;

FIG. 4 is an enlarged front elevational view of one of chucking jigs illustrated in FIG. 2, showing masking liquid after having been discharged onto bar bodies supported by the chucking jig;

FIG. 5 is a top plan view of the chucking jig and the bar body illustrated in FIG. 4;

DETAILED DESCRIPTION

The invention will be described in detail, by way of mere example, with reference to the accompanying drawings.

Figure 1:
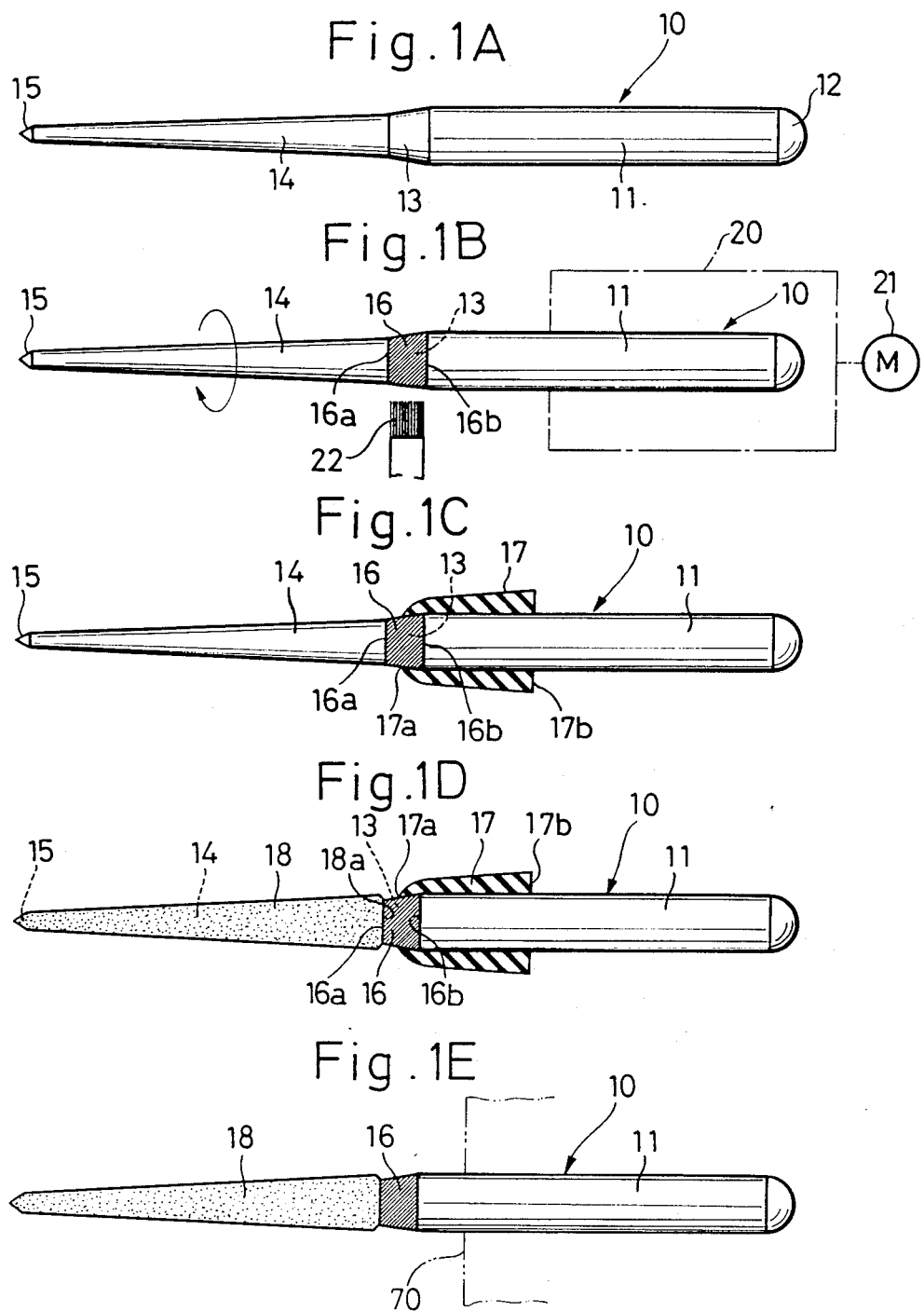
FIGS. 1A through 1E are views showing a dental diamond bar according to an embodiment of the invention, in due order of the sequential steps of procedure of manufacturing the dental diamond bar.

Referring to FIG. 1A, there is illustrated a bar body 10 formed of a steel or a sintered hard alloy. The bar body 10 comprises a columnar shank portion 11 having a circular cross-section. A semi-spherical portion 12 is formed at a rearward end of the shank portion 11. A first tapered portion 13 having a relatively steep gradient extends from the shank portion 11 toward a forward end of the bar body 10. A second tapered portion 14 having a relatively gentle gradient extends from the first tapered portion 13 toward the forward end of the bar body 10. A conical portion 15 is formed at a forward end of the second tapered portion 14. The second tapered portion 14 and the conical portion 15 form a grinding-section scheduled part.

As shown in FIG. 1B, colored paint is applied to the first tapered portion 13 of the bar body 10 to form a paint-applied section 16. The paint has an electrical insulation, and a resistance to organic solvent used in subsequent manufacturing steps. The paint includes, for example, epoxy resin or the like of two-part type in which a primary component and a hardener are mixed with each other.

Application of the paint is effected in the following manner. That is, the shank portion 11 of the bar body 10 is supported by a rotary jig 20. A motor 21 is driven to rotate the bar body 10. While rotating the bar body 10, a brush 22 soaked with the paint is urged against the first tapered portion 13 of the bar body 11. By doing so, application of the paint can be effected simultaneously with measurement of an eccentricity of the axis of the bar body 11, so that it is possible to attempt to improve operating efficiency. Application of the paint by means of the brush 22 enables the paint-applied section 16 to be formed correctly in conformity with the first tapered portion 13 of the bar body 10. The paint-applied section 16 has a forward edge 16a in conformity with the boundary between the first and second tapered portions 13 and 14. A rearward edge 16b of the paint-applied section 16 is in conformity with the boundary between the first tapered portion 13 and the shank portion 11. Both edges 16a and 16b describe complete circles, respectively. Thus, the edges 16a and 16b appear respectively as straight lines, when the bar body 10 is viewed in side elevation.

Subsequently, the paint-applied section 16 is heated and hardened.

Figure 2:
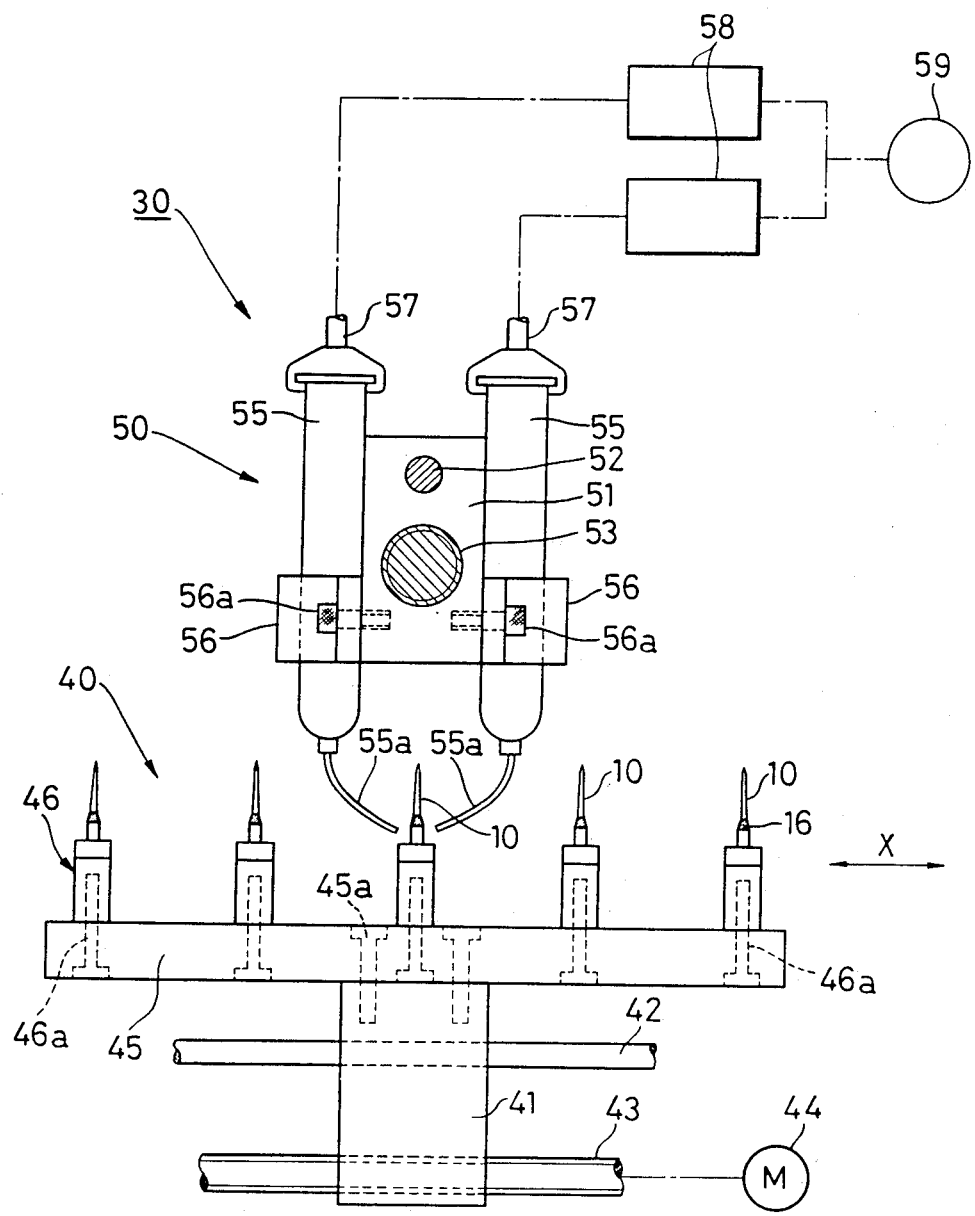
FIG. 2 is a front elevational view of a masking apparatus for use in manufacturing the diamond bar illustrated in FIGS. 1A through 1E.

Subsequently, a masking apparatus 30 shown in FIGS. 2 through 5 is employed to apply masking to the bar bodies 10. As illustrated in FIGS. 2 and 3, the masking apparatus 30 comprises a support device 40 and a masking liquid supply device 50.

The support device 40 has a carriage 41 which is mounted on a guide rod 42 and a screw rod 43 for horizontal movement therealong. As the screw rod 43 is rotatively driven by a motor 44, the carriage 41 is moved horizontally in an X-axis direction as indicated in FIG. 2. A base plate 45 is fixedly mounted on the carriage 41 by means of bolts 45a. A plurality of, e.g. five, elongated chucking jigs 46 are arranged in parallel and spaced relation to each other on an upper surface of the base plate 45. The chucking jigs 46 extend perpendicularly to the moving direction of the carriage 41, i.e., in a Y-axis direction perpendicular to the X-axis direction as indicated in FIG. 3. The chuckling jigs 46 are fixed to the base plate 45 by means of bolts 46a.

Each of the chucking jigs 46 comprises a housing 47 formed therein with a plurality of bores 47a one of which is shown in FIG. 4. The bores 47a are spaced at equal intervals along the housing 47. A cover plate 48 is fixedly mounted on the housing 47. A plurality of resilient electrode plates 49 are arranged respectively within the bores 47a. The housing 47 and the cover plate 48 are formed of an electrically insulating material such as plastics or the like. The cover plate 48 is provided therein with bores 48a corresponding respectively to the electrode plates 49. The shank portions 11 of the respective bar bodies 10 are inserted respectively into the bores 47a in the housing 47 through the respective bores 48a in the cover plate 48, so that the bar bodies 10 are resiliently supported respectively by the electrode plates 49. Lead wires, not shown, are connected respectively to the electrode plates 49. The lead wires are led to a location below the base plate 45 through respective bores 47b (see FIG. 4) formed in the bottom of the housing 47 and through respective bores, not shown, formed in the base plate 45. The chucking jigs 46 shown in FIGS. 2 and 3 are already known from the above-mentioned Japanese Patent Application Laid-Open No. 62-49845. In the Japanese patent, however, the chucking jigs 46 are used in dipping of the bar bodies into masking liquid.

As shown in FIG. 3, a plurality of, e.g. eight, bar bodies 10 are supported by each of the chucking jigs 46. Since the five chucking jigs 46 are arranged on the base plate 45, forty bar bodies 10 in total can be supported on the support apparatus 40.

As will be seen from FIGS. 2 and 3, the masking liquid supply device 50 comprises a carriage 51 which is mounted on a guide rod 52 and a screw rod 53 for horizontal movement therealong. These rods 52 and 53 extend horizontally in the Y-axis direction. As a motor 54 is driven to rotate the screw rod 53, the carriage 51 is moved horizontally along the rods 52 and 53 in the Y-axis direction. A pair of elongated tanks 55 and 55 extending vertically are fixedly mounted respectively to the opposite sides of the carriage 51 by means of respective U-shaped brackets 56 and 56 and respective bolts 56a and 56a. A pair of nozzle tubes 55a and 55a are connected respectively to lower ends of the respective tanks 55 and 55. The nozzle tubes 55a and 55a are bent such that their respective forward end portions are inclined and converge toward each other. Upper ends of the respective tanks 55 and 55 are connected to a common compressed air source 59 through respective flexible tubes 57 and 57 and respective controllers 58 and 58. Each of the tanks 55 is filled with masking liquid which is, for example, a wax or a solution in which natural rubber is diluted with water or organic solvent. The masking liquid has an electric insulation and is relatively high in viscosity. Each of the above-mentioned controllers 58 comprises a selector valve and a pressure regulator for maintaining compressed air to be supplied, at a constant pressure. The elector valve of each of the controllers 58 is so arranged as to permit communication between the compressed air source 59 and a corresponding one of the tanks 55 for a predetermined period of time to supply compressed air from the air source 59 into the corresponding tank 55, thereby discharging a constant amount of masking liquid out of the corresponding tank 55. Subsequently, the selector valve is switched to interrupt the communication between the compressed air source 59 and the corresponding tank 55 and to escape air pressure therewithin to the outside.

While the carriage 41 remains stationary, the carriage 51 is moved in the Y-axis direction. When the carriage 51 is brought to a position where one of the bar bodies 10 is just located between the respective forward ends of the pair of nozzle tubes 55a and 55a, a constant amount of masking liquid is discharged in the manner as described above from each of the nozzle tubes 55a to a corresponding one of the opposite sides of the bar body 10. During such discharge of the masking liquid, the carriage 51 may remain stationary, or may continue to move. As a result, as shown in FIGS. 4 and 5, a masking section 17 is formed about the bar body 10. Position of a forward edge of the masking section 17 with respect to the bar body 10 cannot be made constant for every bar bodies 10, and the forward edge of the masking section 17 waves or undulates. However, as shown in FIG. 1C, the arrangement is such that the position of the forward edge 17a of the masking section 17 is brought to an area between forward and rearward edges 16a and 16b of the above-mentioned paint-applied section 16. In addition, a rearward edge 17b of the masking section 17 is located at an intermediate section of the shank portion 11. The masking section 17 is not formed about a part of the shank portion 11 which is located within the chucking jig 45.

The masking sections 17 are successively formed on the respective bar bodies 10 supported on one of the chucking jigs 46, from the bar body 10 located at the end of the chucking jig 46. Subsequently, the motor 44 is driven to move the carriage 41 in the X-axis direction such that the next chucking jig 46 is aligned with a gap between the pair of nozzle tubes 55a and 55a. Then, masking is successively applied, in a manner like that described above, to the plurality of bar bodies 10 supported on the next chucking jig 46. In this manner, the masking is effected by relative movement between the nozzle tubes 55a and 55a and the bar bodies 10 and by discharging of the masking liquid. Thus, productivity is extremely high, and the consumption amount of the masking liquid can be reduced.

If another masking liquid is used which is lower in viscosity than the above-described masking liquid, each of the nozzle tubes is provided at its base end with a check valve. A pump, which can discharge a constant amount of liquid, may be substituted for the above-described tanks 55 and the compressed air supply system.

After completion of the masking, the base plate 45 is demounted from the carriage 41, and the masking sections 17 are dried and solidified.

Figure 6:
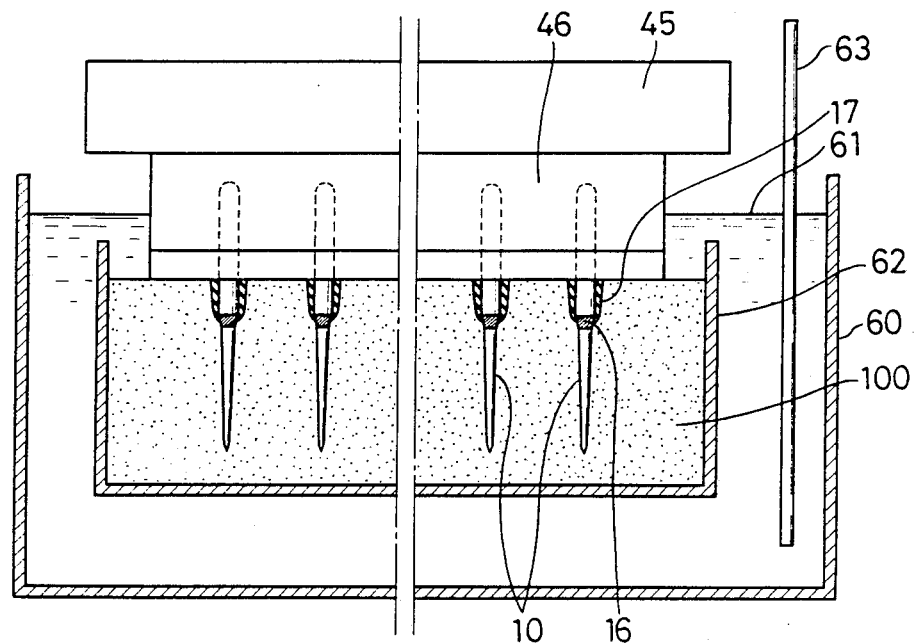
FIG. 6 is a vertical cross-sectional view of an apparatus for electrodepositing diamond abrasive grains onto the bar bodies supported by the chucking jigs illustrated in FIGS. 2 and 3.

Subsequently, electrodeposition of diamond abrasive grains is effected as shown in FIG. 6. Specifically, a tank 60 is filled with electrolytic solution 61 having dissolved therein nickel ions. A container 62 formed of ion permeable ceramics or the like is immersed in the electrolytic solution 61. Diamond abrasive grains 100 are contained in the container 62. The container 62 is supported above the bottom of the tank 60 by means of support members, not shown. A nickel electrode 63 is dipped in the electrolytic solution 61. With the base plate 45 turned upside down, the plurality of bar bodies 10 are driven at a time into the diamond abrasive grains 100. Under such a condition, the nickel electrode 63 is connected to a positive pole of a D.C. power, not shown, and the bar bodies 10 are connected to a negative pole of the D.C. power through the respective electrode plates 49 (see FIG. 4) and the respective lead wires. Then, a shown in FIG. 1D, nickel is deposited and plated on the second tapered portion 14 and the conical portion 15 of each of the bar bodies 10. By this plating layer, the diamond abrasive grains 100 are fixedly bonded to the bar body 10, with the result that a grinding section 18 is formed. It is to be noted that the diamond abrasive grains 100 are not electrodeposited on the paint-applied section 16 and the masking section 17 of the bar body 10.

The grinding section 18 has a rearward edge 18a which is in conformity with the forward edge 16a of the paint-applied section 16, and which is independent of the forward edge 17a of the masking section 17. Accordingly, even if the forward edge 17a of the masking section 17 is inaccurate in position and waves or undulates as described previously, the rearward edge 18a of the grinding section 18 is correctly positioned by the forward edge 16a of the paint-applied section 16, and describes a complete circle so that the rearward edge 18a of the grinding section 18 appears as a straight line when the bar body 10 is viewed in side elevation.

Subsequently, the entire bar body 10 shown in FIG. 1D is immersed in organic solvent such as trichloroethane to dissolve the masking section 17. Thus, a diamond bar is obtained as a final product as shown in FIG. 1E. Since the paint-applied section 16 is formed of epoxy resin and has a resistance to the organic solvent, the paint-applied section 16 is not dissolved in the organic solvent and is not also deteriorated. It is of course that the masking section 17 can be removed manually from the bar body 10. In this case, it is possible to use paints having no resistance to the organic solvent.

With the diamond bar manufactured as described above, even if the shank portion 11 is inserted into the handpiece 70 as shown in FIG. 1E, the colored paint-applied section 16 adjacent the grinding section 18 is located on the outside of the handpiece 70. Accordingly, it is possible to advise a user of information concerning the type or kind of the diamond bar such as the configuration of the grinding section 18, the particle size of the diamond abrasive grains, and the like. The same can be said also in case where the shank portion 11 is inserted into the storage bar stand.

Figure 7:
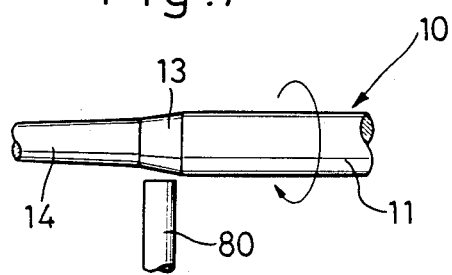
FIG. 7 is a fragmental front elevational view showing a manner of applying colored paint to a bar body, the applying manner being different from that shown in FIG. 1B.

Application of the colored paint may be effected in a manner as shown in FIG. 7. That is, a constant amount of colored paint is injected from a nozzle tube 80 having a small diameter, toward the first tapered portion 13 of the bar body 10 while rotating the latter.

Figure 8:
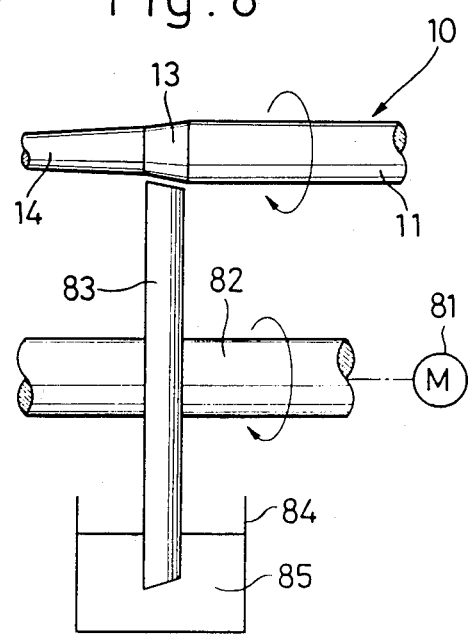
FIG. 8 is a view similar to FIG. 7, but showing still another manner of application of colored paint.

Application of the colored paint may also be effected in a manner as shown in FIG. 8. That is, a rotary blade 83 is fixedly mounted on a shaft 82 which is adapted to be rotatively driven by a motor 81. The blade 83 has an outer peripheral surface in a frustoconical shape corresponding to the first tapered portion 13 of the bar body 10. The blade 83 has a lower portion which is immersed in colored paint 85 contained in a container 84. The bar body 10 is rotated about an axis in parallel to the shaft 2. The rotary blade 83 is rotated at a speed lower than that of the bar body 10. The colored paint 85 adheres to the peripheral surface of the rotary blade 83. Accordingly, as the bar body 10 rotates, the colored paint 85 is applied to the entire peripheral surface of the first tapered portion 13.

A rod-like blade may be substituted for the brush 22 shown in FIG. 1B. In this case, colored paint adhering to the tip of the rod-like blade is applied to the first tapered portion 13 of the bar body 10.

Figure 9:
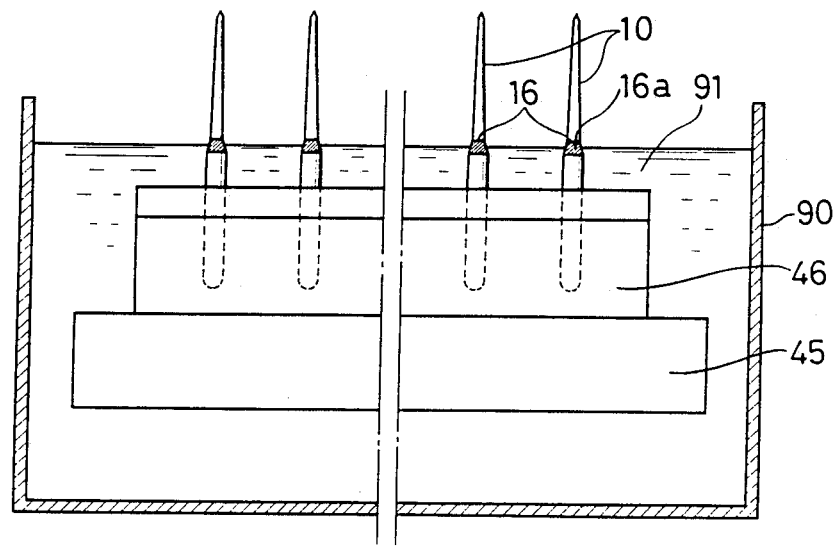
FIG. 9 is a view similar to FIG. 6, but showing another masking manner.

FIG. 9 shows another embodiment of the invention, in which a dipping technique is employed in substitution for the masking liquid discharging technique shown in FIGS. 2 through 5. In the embodiment illustrated in FIG. 9, masking liquid 91 is contained in a tank 90. A plurality of bar bodies 10 are immersed, together with the base plate 45 and the chucking jigs 46, in the masking liquid 91 in such a manner that the forward end portions of the respective bar bodies 10 project upwardly from the surface level of the masking liquid 91. Although the surface level of the masking liquid 91 is unstable, the arrangement is such that the surface level of the masking liquid 91 is always brought to an area between the forward and rearward edges 16a and 16b of the colored paint-applied section 16 of each of the bar bodies 10. The dipping technique is also extremely high in efficiency, like the above-described masking liquid discharging technique. In addition, even if the forward edge of the masking section is unstable in position and waves or undulates, no bad influence is exerted on formation of the grinding section, because the rearward edge of the grinding section can be determined by the forward edge 16a of the paint-applied section 16.

Figure 10:
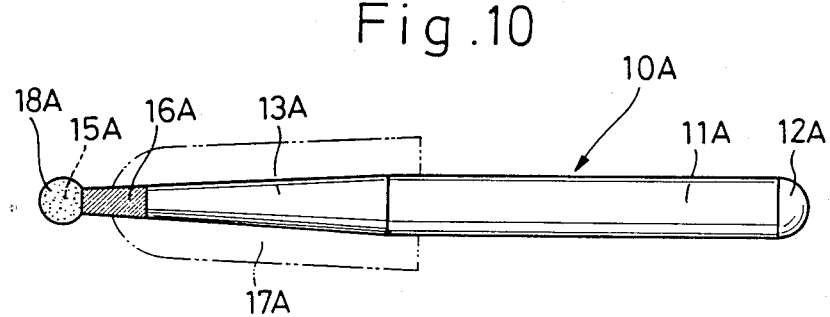
FIG. 10 is a side elevational view of another configuration of the dental diamond bar according to the invention.

FIG. 10 shows another configuration of the dental diamond bar. A bar body 10A has a shank portion 11A, and a semi-spherical portion 12A located at a rearward end of the shank portion 11A. A tapered portion 13A extends from the shank portion 11A toward a forward end of the bar body 10A. A spherical portion 15A is provided at a forward end of the tapered portion 13A. A colored paint-applied section 16A having a predetermined axial width is first formed on the forward end of the tapered portion 13A. A masking section 17A is then formed by the use of any one of the above-described masking techniques. Subsequently, a grinding section 18A is formed on the spherical portion 15A. Finally, the masking section 17A is removed. In case of the diamond bar according to the embodiment shown in FIG. 10, a metallic substrate of the bar body 10A is exposed at a rearward end part of the tapered portion 13A, the shank portion 11A and the semispherical portion 12A.

Figure 11:
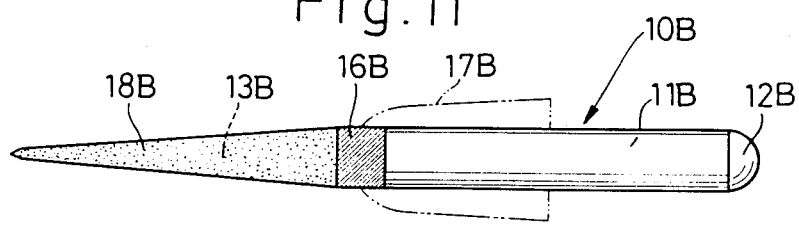
FIG. 11 is a view similar to FIG. 10, but showing still another configuration of the dental diamond bar.

FIG. 11 shows still another configuration of the diamond bar. A bar body 10B has a shank portion 11B, and a semi-spherical portion 12B provided at a rearward end of the shank portion 11B. A tapered portion 13B extends from the shank portion 11B to a forward end of the bar body 10B. A colored paint-applied section 16B having a predetermined axial width is first formed about a forward end part of the shank portion 11B. A masking section 17B is then formed. Subsequently, a grinding section 18B is formed on the entire tapered portion 13B. Finally, the masking section 17B is removed.

It is of course that the part of the bar body, on which the grinding section is to be formed, may be columnar in shape having a circular cross-section, or may have any other configuration.

The masking section may be formed on substantially the entire area of a part of the bar body which extends from the paint-applied section to the rearward end of the bar body, except for a part to which an electrode is to be connected.

What is claimed is:

1. A method of manufacturing a dental diamond bar comprising the steps of:

applying an electrically insulating colored paint to an outer peripheral surface of an intermediate section of a bar body to form a paint-applied section so as to bring said paint-applied section correctly into conformity with a predetermined axial area on said intermediate section;

applying masking liquid formed of an electrical insulating material to said bar body, and solidifying the masking liquid to form a masking section, said masking section having a forward edge located between forward and rearward edges of said paint-applied section, said masking section extending toward a rearward end of said bar body;

fixedly bonding diamond abrasive grains to a part of said bar body extending from the forward edge of said paint-applied section to a forward end of said bar body, by an electrodeposition technique, to form a grinding section; and removing said masking section after formation of said grinding section.

2. A method as defined in claim 1, wherein the colored paint is applied to said bar body while rotating the latter, to form said paint-applied section.

3. A method as defined in claim 2, wherein the colored paint is applied by a brush to said bar body to form said paint-applied section.

4. A method as defined in claim 2, wherein the colored paint is injected from a nozzle to apply the colored paint to said bar body.

5. A method as defined in claim 2, wherein the colored paint is caused to adhere to a peripheral surface of a rotary body rotating about an axis in parallel to an axis of said bar body, and the colored paint is applied from said rotary body to a part of said bar body adjacent the peripheral surface of said rotary body.

6. A method as defined in claim 1, wherein a rearward end portion of said bar body is inserted into chucking jig means such that said bar body stands up from said chucking jig means, a pair of nozzle tubes of a masking liquid supply device are arranged respectively at opposite sides of said bar body, and a constant amount of masking liquid is discharged from each of said pair of nozzle tubes toward said bar body to form said masking section.

7. A method as defined in claim 6, wherein a plurality of bar bodies are supported in a row on said chucking jig, and relative movement is caused along the row of said bar bodies between said chucking jig and said masking liquid supply device to successively locate said bar bodies at a position between said pair of nozzle tubes.

8. A method as defined in claim 1, wherein said bar body is dipped in the masking liquid such that a forward end portion of said bar body projects upwardly from a surface level of the masking liquid, to apply the masking liquid to said bar body, the surface level of the masking liquid being located between the forward and rearward edges of said paint-applied section.

9. A method as defined in claim 8, wherein a plurality of bar bodies are supported on chucking jig means, and the bar bodies together with said chucking jig means are dipped in the masking liquid.

10. A method as defined in claim 1, wherein said paint-applied section is formed by a paint having a resistance to organic solvent, and said masking section is removed by the organic solvent after formation of said grinding section.

* * * * *